(12) United States Patent
Strohmeier et al.

(10) Patent No.: US 8,951,417 B2
(45) Date of Patent: Feb. 10, 2015

(54) METHOD OF TRANSPORTING MAGNETIC PARTICLES

(71) Applicant: Hahn-Schickard-Gesellschaft fuer angewandte Forschung e.V., Villingen-Schwenningen (DE)

(72) Inventors: Oliver Strohmeier, Freiburg (DE); Felix Von Stetten, Freiburg-Tiengen (DE); Daniel Mark, Freiburg (DE)

(73) Assignee: Hahn-Schickard-Gesellschaft fuer angewandte Forschung e.V, Villingen-Schwenningen (DE)

( * ) Notice: Subject to any disclaimer, the term of this patent is extended or adjusted under 35 U.S.C. 154(b) by 133 days.

(21) Appl. No.: 13/852,367

(22) Filed: Mar. 28, 2013

(65) Prior Publication Data

US 2013/0206701 A1 Aug. 15, 2013

Related U.S. Application Data

(63) Continuation of application No. PCT/EP2011/066672, filed on Sep. 26, 2011.

(30) Foreign Application Priority Data

Sep. 29, 2010 (DE) .......................... 10 2010 041 621

(51) Int. Cl.
*B03C 1/00* (2006.01)
*B03C 1/02* (2006.01)
(Continued)

(52) U.S. Cl.
CPC ............. *B03C 1/02* (2013.01); *B01L 3/502761* (2013.01); *G01N 35/00069* (2013.01); *B81B 1/00* (2013.01); *B01L 2200/0668* (2013.01); *B01L 2300/087* (2013.01); *B01L 2300/0883* (2013.01); *B01L 2400/0409* (2013.01); *B01L 2400/043* (2013.01)
USPC ............. 210/695; 210/781; 210/806; 436/45; 436/177

(58) Field of Classification Search
USPC ............. 210/695, 781, 806, 223; 436/45, 177
See application file for complete search history.

(56) References Cited

U.S. PATENT DOCUMENTS

| 5,252,493 A | 10/1993 | Fujiwara et al. |
| 6,117,630 A | 9/2000 | Reber et al. |

(Continued)

FOREIGN PATENT DOCUMENTS

| DE | 103 55 460 A1 | 6/2005 |
| EP | 0 344 276 B1 | 6/1993 |

(Continued)

OTHER PUBLICATIONS

The International Preliminary Report on Patentability for PCT/EP2011/066672, Feb. 19, 2013.*

(Continued)

*Primary Examiner* — David A Reifsnyder
(74) *Attorney, Agent, or Firm* — Keating & Bennett, LLP

(57) ABSTRACT

A method of transporting magnetic particles enables magnetic particles to be transported between a plurality of microfluidic chambers which are connected to one another via a fluidic connection on a radially inner side, and are fluidically separated from one another on a radially outer side. Magnetic forces and centrifugal forces are exploited to transport magnetic particles from one chamber to another across phase boundaries.

10 Claims, 2 Drawing Sheets

(51) Int. Cl.
*B81B 1/00* (2006.01)
*G01N 35/00* (2006.01)
*B01L 3/00* (2006.01)

(56) References Cited

U.S. PATENT DOCUMENTS

| | | | |
|---|---|---|---|
| 8,313,652 B2 * | 11/2012 | Hein et al. | 210/695 |
| 2005/0242091 A1 | 11/2005 | Bedingham et al. | |
| 2007/0114229 A1 | 5/2007 | Bedingham et al. | |
| 2007/0129542 A1 | 6/2007 | Ahmad et al. | |
| 2008/0035579 A1 | 2/2008 | Lee et al. | |
| 2008/0073546 A1 | 3/2008 | Andersson et al. | |
| 2008/0108120 A1 | 5/2008 | Cho et al. | |
| 2008/0171400 A1 | 7/2008 | Cho et al. | |
| 2008/0314895 A1 | 12/2008 | Bedingham et al. | |
| 2009/0246782 A1 | 10/2009 | Kelso et al. | |
| 2009/0269854 A1 | 10/2009 | Kageyama | |

FOREIGN PATENT DOCUMENTS

| | | | |
|---|---|---|---|
| EP | 1 533 605 A3 | 5/2006 | |
| EP | 1 901 054 A2 | 3/2008 | |
| EP | 2 026 074 A2 | 2/2009 | |
| JP | 2009-148735 A | 7/2009 | |
| WO | 2007/106013 A1 | 9/2007 | |
| WO | 2011/015454 A1 | 2/2011 | |
| WO | WO 2012041809 A1 * | 4/2012 | |

OTHER PUBLICATIONS

Official Communication issued in International Patent Application No. PCT/EP2011/066672, mailed on Nov. 23, 2011.

Grumann et al., "Batch-mode mixing on centrifugal microfluidic platforms", The Royal Society of Chemistry, Lab on a Chip, vol. 5, 2005, pp. 560-565.

Manz et al., "Miniatrurized Total Chemical-Analysis Systems; a Novel Concept for Chemical Sensing", Elsevier Sequoia, Sensors and Actuators, B1, 1990, pp. 244-248.

Ducree et al., "The centrifugal microfluidoc Bio-Disk platform," Journal of Micromechanics and Microengineering, Jun. 28, 2007, pp. s103-s115.

Haeberle et al., "Microfluidic Platforms for Lab-on-a Chip Applications", The Royal Society of Chemistry, Lab on a Chip, vol. 7, No. 9, Sep. 2007, pp. 1081-1220.

Cho et al., "One-step pathogen specific DNA extraction from whole blood a centrifugal microfluidic device", The Royal Society of Chemistry, Lab on a Chip, vol. 7, 2007, pp. 565-573.

* cited by examiner

METHOD OF TRANSPORTING MAGNETIC PARTICLES

CROSS-REFERENCE TO RELATED APPLICATIONS

This application is a continuation of copending International Application No. PCT/EP2011/066672, filed Sep. 26, 2011, which is incorporated herein by reference in its entirety, and additionally claims priority from German Application No. 102010041621.5, filed Sep. 29, 2010, which is also incorporated herein by reference in its entirety.

BACKGROUND OF THE INVENTION

The present invention relates to a method of transporting magnetic particles, and in particular to a method of transporting magnetic particles from a first liquid into a second liquid, which is not significantly in fluidic contact with the first liquid.

Microfluidic systems are becoming increasingly important, in particular in the fields of medicinal and molecular diagnostics applications, the term µTAS (micro total analysis system), among others, having been coined for such systems. Please see, for example, A. Manz, N. Graber, and H. M. Widmer, "Miniaturized Total Chemical-Analysis Systems—A Novel Concept for Chemical Sensing," Sensors and Acutators B-Chemical, Vol. 1, No. 1—6, pp. 244-248, January 1990.

In this context, microfluidic systems are of great interest since, due to their high surface/volume ratios, short diffusion paths and minimal reagent volumes, (bio)chemical reactions may proceed at increased velocity. At the same time, corresponding systems have comparatively low space and energy requirements. Due to said features, microfluidic systems are suited in particular for time-critical applications and so-called field diagnostics.

Potential fields of application of microfluidic systems include the entire range of molecular biology applications, for example DNA analytics, protein analytics, cell analytics and clinical chemistry. Numerous approaches to realizing such systems have been described in literature. The central differentiation criterion in this context essentially is the principle of actuating the liquids. In addition to pressure- and capillary-operated systems, in particular centrifugal-microfluidic systems, wherein liquids may be moved and switched on a corresponding platform by means of defined rotation on account of centrifugal forces, are important. Such systems are known by the designation "Lab-on-a-Disk". In this context, please refer to J. Ducrée, S. Lutz, S. Pausch, F. v. Stetten and R. Zengerle, "The centrifugal microfluidic Bio-Disk platform, J. Micromech. Microeng., Vol. 17, No. 7, p 103-p. 115, 2007, and S. Haeberle and R. Zengerle, "Microfluidic Platforms for Lab-on-a-Chip Applications," Review Paper in "Lab on a Chip" Journal, Vol. 7, No. 9, pp. 1094-1110, 2007.

In the field of biochemical analytics, magnetic particles having diameters that lie within nano- and micrometer ranges, which are also referred to as magnetic beads, are a popular and widely applicable material. They are used for transporting, mixing, separating and concentrating biological molecules and cells, for example DNA, antibodies or bacteria, or for performing heat transfer: depending on the type of application, the surfaces of the magnetic particles may be modified accordingly.

M. Grumann, A. Geipel, L. Riegger, R. Zengerle, and J. Ducrée, "Batch-mode-mixing on centrifugal microfluidic platforms," Lab Chip, Vol. 5, pp. 560-565, 2005 describes utilization of magnetic particles in a centrifugal system to improve intermixing of two liquids within a chamber. The chamber comprising the magnetic particles rotates past eight stationary permanent magnets. Once the particles are within the sphere of influence of the magnetic field, they are set in motion, whereby intermixing of two liquids is improved considerably. The particles are stationary within a chamber.

Y. K. Cho, J. G. Lee, J. M. Park, B. S. Lee, Y. Lee, and C. Ko, "One-step pathogen specific DNA extraction from whole blood on a centrifugal microfluidic device," Lab Chip, Vol. 7, pp. 565-573, February 2007, and U.S. 2008/0035579 A1 describe a Lab-on-a-Disk system which employs magnetic particles coated with antibodies to obtain bacteria and viruses from a sample material and to wash and isolate them. For the purpose of localized manipulation of the magnetic particles, a magnet is located on a linear axis underneath the rotating disk of the system, while a second, movable magnet is located within the disk body. Depending on the direction of rotation and the speed as well as on the position of the magnet underneath the disk, the magnet located within the disk body may take on four different positions and thus actively move the particles and/or fix them at a specific position within the disk.

U.S. 2008/0073546 A1 describes a method of improved mixing within microfluidics structures while using magnetic particles. At rotational frequencies below a critical rotational frequency, particles are drawn inward in a radial direction by the dominant magnetic force of externally mounted permanent magnets, whereas at rotational frequencies above the critical rotational frequency, the centrifugal force predominates over the magnetic force, and the particles are spun outward in the radial direction. By suitably selecting the rotational frequency and the rotational direction, different "mixing patterns" may thus be produced. In addition, the possibility of transporting magnetic particles within the mixing chamber into a particle pocket wherein the particles are caught in a stationary manner is described. Moreover, the particles may also be transported, within the liquid, into a particle pocket mounted, in radial terms, above a second pocket. By means of a corresponding protocol, the particles may be centrifuged, together with a supernatant of liquid, into a second chamber which is located further outward in the radial direction. In this context, mention is made that the particles may be employed as solid-phase carriers for performing an assay (for example an immunoassay).

U.S. 1009/0246782 A1 describes a possibility of transporting paramagnetic particles between different chambers. The gap in between the chambers has to be filled with a lipophilic, water-insoluble material through which the particles are transported. Possible materials that meet said conditions are, for example, silicone oils or corresponding waxes. The magnetic particles are actively manipulated using an actuatable magnet and are transported through the individual liquid phases.

U.S. 2008/0171400 A1 discloses a system for locally fixing magnetic particles within a radially outer channel loop of a centrifugal-microfluidic platform. The magnetic particles are fixed by a co-rotating magnet, so that it is possible to sequentially flush individual reagents over the particles.

U.S. 2007/0125942 A1 describes a system for mechanically lyzing, separating and isolating biological materials. Lysis is achieved by means of at least one movable magnetic disk and glass particles within the lysis chamber. To produce a locally fluctuating magnetic field, the disk comprising the chambers rotates past an array of radially inner and outer magnets.

SUMMARY

According to an embodiment, a method of transporting magnetic particles while using a device may have: a rotational body configured for a rotation about an axis of rotation; a fluidics structure within the rotational body, said fluidics structure having at least first and second fluid chambers, the first and second fluid chambers having a fluidic connection in a portion which is located radially inward in relation to the axis of rotation, and being fluidically separated from each other in a portion which is located radially outward in relation to the axis of rotation; and a permanent magnet configured to exert, as a function of a positional relationship between the magnetic-force element and the fluidics structure, a magnetic force on magnetic particles arranged in the fluidics structure; and a drive configured to subject the rotational body to rotation about the axis of rotation, the positional relationship between the permanent magnet and the fluidics structure being adjustable as a result, the method may have the steps of: in a first phase, arranging the first fluid chamber in relation to the permanent magnet in such a manner that, due to the magnetic force, the magnetic particles are transported from a liquid arranged in the radially outer portion of the first fluid chamber into the radially inner portion of the first fluid chamber; in a second phase, changing the positional relationship between the fluidics structure and the permanent magnet by rotating the rotational body such that, due to the magnetic force, the magnetic particles are transported through the fluidic connection between the first and second fluid chambers into the radially inner portion of the second fluid chamber; and in a third phase, subjecting the rotational body to such rotation that the magnetic particles are transported, by means of centrifugal force, from the radially inner portion of the second fluid chamber into a liquid arranged in the radially outer portion of the second fluid chamber, said liquid not being in fluidic contact with the liquid in the first fluid chamber, wherein in the first phase, the magnetic particles are transported across a phase boundary between the liquid in the radially outer portion of the first fluid chamber and a gas in the radially inner portion of the first fluid chamber, and wherein in the third phase the magnetic particles are moved across a phase boundary between a gas in the radially inner portion of the second fluid chamber and the liquid in the radially outer portion of the second fluid chamber, wherein the adjustment of the positional relationship of the permanent magnet and the fluidics structure, which results in the transport of the magnetic particles due to the magnetic force, is effected by rotating the rotational body.

In addition, the present invention provides a method of transporting magnetic particles by means of a device comprising: a rotational body configured for a rotation about an axis of rotation; a fluidics structure within the rotational body, said fluidics structure comprising at least first and second fluid chambers, the first and second fluid chambers comprising a fluidic connection in a portion which is located radially inward in relation to the axis of rotation, and being fluidically separated from each other in a portion which is located radially outward in relation to the axis of rotation; and a magnetic-force element configured to exert, as a function of a positional relationship between the magnetic-force element and the fluidics structure, a magnetic force on magnetic particles arranged in the fluidics structure; and a drive configured to subject the rotational body to rotation about the axis of rotation, the positional relationship between the magnetic-force element and the fluidics structure being adjustable as a result, the method comprising: in a first phase, arranging the first fluid chamber in relation to the magnetic-force element in such a manner that, due to the magnetic force, the magnetic particles are transported from a liquid arranged in the radially outer portion of the first fluid chamber into the radially inner portion of the first fluid chamber; in a second phase, changing the positional relationship between the fluidics structure and the magnetic-force element such that, due to the magnetic force, the magnetic particles are transported through the fluidic connection between the first and second fluid chambers into the radially inner portion of the second fluid chamber; and in a third phase, subjecting the rotational body to such rotation that the magnetic particles are transported, by means of centrifugal force, from the radially inner portion of the second fluid chamber into a liquid arranged in the radially outer portion of the second fluid chamber, said liquid not being in fluidic contact with the liquid in the first fluid chamber.

In embodiments of the invention, an interplay of magnetic forces and centrifugal forces is exploited to transport magnetic particles out of a first liquid and to transport them into a second liquid. In embodiments of the invention, particles may be transported, by magnetic force, across a liquid/gas phase boundary into a radially inner portion of a fluid chamber, and may subsequently be transported, by centrifugal forces, from a radially inner portion of a fluid chamber across a gas/liquid phase boundary and into a liquid. Thus, embodiments of the invention enable magnetic particles, which may also be referred to as beads, to be transported between a plurality of microfluidic chambers, which may be located on a centrifugal-microfluidic platform. Fluid chambers between which the particles are to be transported are interconnected, on a radially inner side, via a fluidic connection which may be formed by a gap. The fluidic connection may be filled with a gas, for example air. Embodiments of the present invention thus provide a transport mechanism which enables particles to be transported, in a manner that is free from cross-contamination, across variable phase boundaries such as liquid/liquid phase boundaries or liquid/gas phase boundaries, for example.

Embodiments of the invention are thus based on an interaction of inertial and magnetic forces on a rotational body, for example a rotating substrate, and a stationary permanent magnet arranged in a certain manner, and allow, for the first time, magnetic particles to be transported between different, e.g. iso-radially arranged, chambers on the substrate across a liquid/gas interface. In addition to the drive for the rotational body, no additional actuation units and/or magnets are necessitated in the substrate for transporting the particles. This results in advantages in the manufacture with correspondingly lower cost and accelerated sequence operations in the implementation of biochemical protocols. Embodiments of the invention are suited, in particular, for unspecific DNA extraction by means of magnetic particles on a centrifugal-microfluidic platform. The inventive transport mechanism is thus suited, in particular, for many centrifugal-microfluidic diagnostics applications.

Embodiments of the invention are suited, in particular, for microfluidic systems. "Microfluidic" systems may be understood to mean such systems which comprise fluidics structures having at least characteristic cross-sectional dimensions within the micrometer range or sub-micrometer range, and/or such systems that are suited for transporting and processing volumes of liquid that are within the microliter range or sub-microliter range. In embodiments of the invention, the fluid chambers are iso-radially arranged, i.e. they completely overlap in the azimuthal direction. In alternative embodiments, the fluid chambers have areas that overlap at least in the azimuthal direction.

Unlike the conventional technology described, embodiments of the invention have numerous advantages. For example, according to U.S. 2008/0073546 A1, particles can only be moved within the same liquid phase, which necessitates that a second chamber has to be located further outward, in radial terms, as compared to the first chamber, so that more space will be necessitated in the radial direction. In addition, according to U.S. 2008/0073546 A1 for flushing the particles the valve with the particle trap has to be designed in such a robust manner that any reagents used may be retained during the mixing process, irrespective of their fluidic properties. Embodiments of the present invention avoid such disadvantages since such valves are not necessitated. In addition, according to U.S. 2008/0073546 A1, a substantial carry-over of liquid between the chambers takes place. In particular with highly sensitive biological assays (such as immunoassays, polymerase chain reaction, melting curve analysis, for example) even minor cross-contamination may lead to incorrect results or in complete failure of the assay. In embodiments of the invention, cross-contamination between different liquids may be reliably avoided. The method shown in U.S. 2008/0073546 A1 necessitates high rotational frequencies for mixing the magnetic particles as well as rotations in the clockwise and counter-clockwise directions, which increases the requirements in terms of the drive. Embodiments of the invention merely necessitate rotations in one rotational direction.

Embodiments of the present invention combine centrifugal force and magnetic force in an advantageous manner in order to transport magnetic particles between liquids. Immiscible separation phases as are necessitated according to U.S. 2009/0246782 A1 are not mandatory in embodiments of the present invention, since the liquids may also be fluidically separated by gas, such as air.

The present invention enables marked simplifications as compared to U.S. 2008/0171400 A1, since according to said document, a magnet has to co-rotate and since the lysis and washing liquids flushed over the fixed particles have subsequently to be fluidically separated off from the eluate, for which purposes a switch is necessitated. Movable magnets in the disk has to be disposed of together with the disk, which results in higher cost and in increased production expenditure since the magnets have to be introduced during production. In addition, according to U.S. 2008/0171400 A1, the process chambers are arranged to be successive in the radial direction, so that important space is occupied in particular in the radial direction. Subsequent process steps are difficult or impossible to perform. Similarly, even according to U.S. 2007/0125942 A1, the chambers are arranged in the radial direction, and all of them are in fluidic contact, which increases cross-contamination. Moreover, in this case, no transport of particles takes place, but the particles mainly serve to generate shear forces within the lysis chamber.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
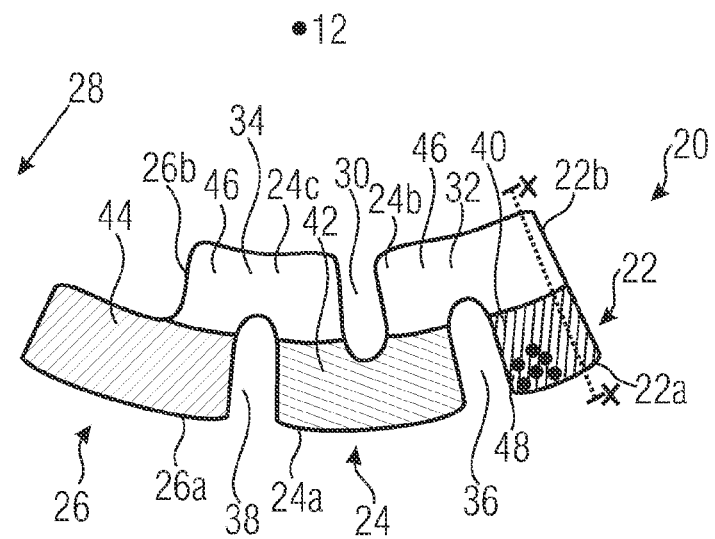
FIG. 1 shows a schematic top view of a fluidics structure of an embodiment of an inventive device.

With regard to FIGS. 1 and 2, an embodiment of an inventive device for transporting magnetic particles will be explained in more detail below. The device includes a rotational body 10, for example in the form of a disk. Alternatively, the rotational body 10 might be formed by an insert that may be inserted into a rotational body, for example a disk. The rotational body 10 is rotatable about an axis of rotation 12, only the left-hand side of the rotational body 10 being fully depicted in FIG. 2. Via a coupling means 14, the rotational body 10 is coupled to a motor 16, which represents a drive for the rotational body 10. The coupling means may be structured in a common manner known to persons skilled in the art. The motor 16 is connected to a controller 18 designed to control the motor 16 in order to allow magnetic particles to be transported in the inventive manner. The controller may be implemented in hardware or in software and may be configured to provide suitable drive signals for the motor. The manner in which a corresponding controller may be configured is known to persons skilled in the art and does not necessitate any further explanation herein.

The rotational body 10 has a fluidics structure 20 provided therein. For example, the fluidics structure 20 may be formed by a recess in part of the rotational body 10 and may be covered by a cover unit.

The fluidics structure 20 comprises a first fluid chamber 22, a second fluid chamber 24, and a third fluid chamber 26. The fluid chambers each have radially inner and radially outer portions, in relation to the axis of rotation 12 in each case, a radially outward direction being indicated by an arrow 28 in FIG. 1. More specifically, the first fluid chamber 22 has a radially outer portion 22a and a radially inner portion 22b. The second fluid chamber 24 has a radially outer portion 24a and a radially inner portion, which is separated into a first radially inner area 24b and a second radially inner area 24c by a barrier 30. The third fluid chamber 26 has a radially outer area 26a and a radially inner area 26b. The radially inner portion 22b of the first fluid chamber 22 is connected to the radially inner area 24b of the second fluid chamber 24 by a fluidic connection 32. The radially inner area 24c of the second fluid chamber 24a is fluidically connected to the radially inner portion 26b of the third fluid chamber 26 via a fluidic connection 34. The radially outer portions 22a and 24a of the first fluid chamber 22 and the second fluid chamber 24 are fluidically separated by a barrier 36, and the radially outer portions 24a and 26a of the second and third fluid chambers 24 and 26 are fluidically separated by a barrier 38. As is shown in FIG. 1, a first liquid 40 is arranged within the radially outer portion 22a of the first fluid chamber 22, a second liquid 42 is arranged in the radially outer portion 24a of the second fluid chamber 24, and a third liquid 44 is arranged in the radially outer portion 26a of the third fluid chamber 26.

A gas 46, for example air, is arranged in each of the radially inner portions 22b, 24b, 24c, and 26b, as is also shown in FIG. 1. In addition, magnetic particles 48 are arranged in the first liquid 40 in the radially outer portion 22a of the first fluid chamber 22.

Figure 2:
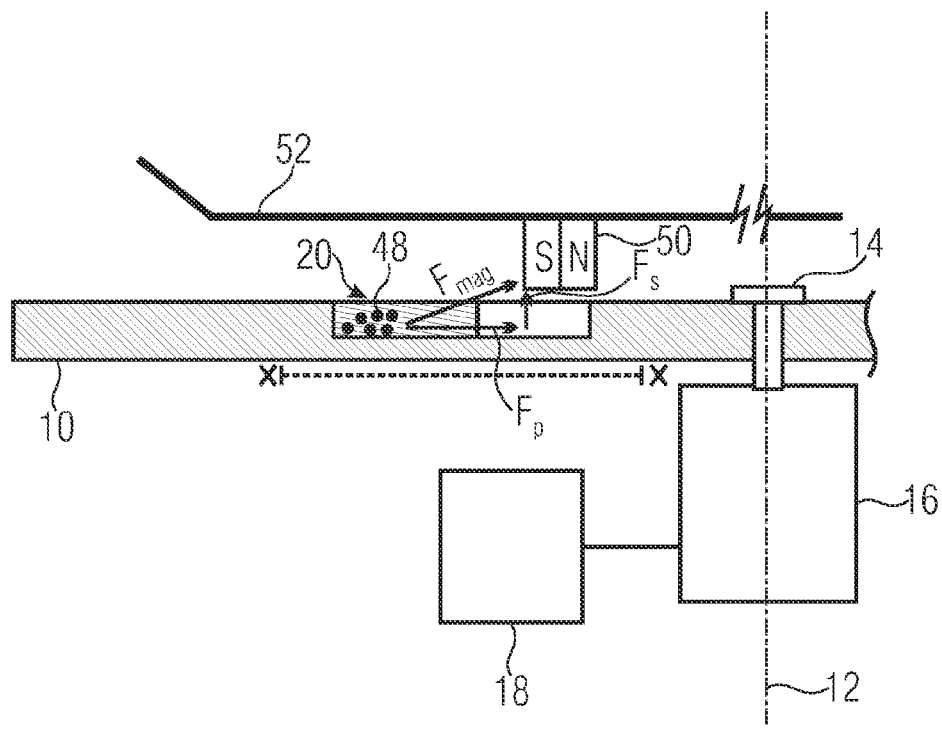
FIG. 2 schematically shows a cross-sectional view of an embodiment of an inventive device.

It shall be noted at this point that FIG. 2 depicts a section through the rotational body along the line x-x in FIG. 1, so that that part of the fluidics structure 2 which can be seen in FIG. 2 represents the first fluid chamber 22.

As is shown in FIG. 2, a magnet 50, which represents a magnetic-force element, is arranged in a stationary manner above the rotational body 10. The magnet 50 may be mounted at the bottom of a centrifuge cover 52, for example. By rotating the rotational body 10 by means of the drive 16 under the control of the controller 18, the positional relationship of the magnet 50 to the fluidics structure 22 may be changed. Thus, the magnetic particles 48 may be transported out of the first liquid 40 into the second liquid 42 and then into the third liquid 44, as will be explained below in more detail with reference to FIG. 3.

The magnet 50 is located above the rotational body at a suitable distance so as to be able to exert a suitable magnetic force on the magnetic particles 48. If the first fluid chamber 22 is positioned in relation to the magnet 50 in the manner shown in FIG. 2, the magnetic force $F_{mag}$, which is shown in FIG. 2 and has a component $F_p$ parallel to the main surfaces of the rotational body 10 (radially inward) and a component $F_s$ perpendicular to the main surfaces of the rotational body, will act on the magnetic particles 48. As a result, it is possible to exert a radially inwardly directed force on the magnetic particles 48 by suitably positioning the fluidics structure, with the magnetic particles 48 contained therein, in relation to the magnet 50. If this inwardly directed magnetic force predominates over an outwardly directed centrifugal force (for example if there is no rotation), the magnetic particles will move inward in the radial direction. If the outwardly directed centrifugal force predominates, for example during rotation at a sufficiently high rotational speed, the outwardly directed centrifugal force will predominate. In embodiments of the invention, this fact is exploited to transport the magnetic particles through several liquids.

Different phases of such a transport in accordance with an embodiment of the invention are shown in FIGS. 3a-3f. FIG. 3a shows a phase 0, which represents an initial state wherein the rotational body is rotated in the clockwise direction (arrow 54) at such a rotational speed that the magnetic particles are retained, due to the centrifugal force, in the radially outer portion 22a of the first fluid chamber 22, specifically, due to their inertia, in an area of same which is located rearward in the rotational direction. Due to the centrifugal force, the liquids 40, 42 and 44 are also retained in the radially outer portions of the respective fluid chambers 22, 24 and 26. Starting from phase 0, the rotational body is stopped, as is shown in FIG. 3b, in a defined position relative to the magnet 50 in a phase 1, so that the magnet 50 will be arranged adjacently to the radially inner portion 22b of the first fluid chamber 22. Due to the magnetic force caused by the magnet 50, the magnetic particles 48 move radially inward toward the magnet 50 and are thus transported into the radially inner portion 22b of the first fluid chamber 22. The magnetic force caused by the magnet 50 is sufficient for the agglomerate consisting of the magnetic particles 48 to be able to cross the interface between the liquid 40 and the air 46.

Starting from the state shown in FIG. 3b, the rotational body is incrementally moved in the counter-clockwise direction in a phase 2, as is schematically shown by arrows 56 in FIG. 3c. The incremental rotation 56 is configured such that the rotational body continues to move in the counter-clockwise direction in small steps, so that the magnetic particles 48 will follow the magnet 50 in this movement. Consequently, the magnetic particles 48 are transported into the radially inner area 24b of the second fluid chamber 24 via the fluidic connection 32. It is obvious to persons skilled in the art that to this end the surface of the fluidics structure along which the magnetic particles 48 move is to be configured in a suitable manner, for example to be sufficiently smooth, in order to enable a corresponding movement.

Starting from the state as is shown in FIG. 3c, the rotational body is again subject to rotation in the counter-clockwise direction in a phase 3, as is indicated by an arrow 58 in FIG. 3d. The rotational frequency is sufficient to cause the magnetic particles to be transported into the radially outer portion 24a of the second fluid chamber 24 by the centrifugal force caused thereby. Since, with such a rotation, the fluidics structure passes the magnet 50 only briefly in each case, low rotational frequencies may already be sufficient to transport the magnetic particles into the radially outer portion 24a of the second fluid chamber 24. Starting from the state shown in FIG. 3d, the magnetic particles 48 accumulate, due to their inertia, in an area of the radially outer portion 24a which is located rearward in the rotational direction, i.e. in an area that is adjacent to the radially inner area 24c of the second fluid chamber 24. Thus, in phase 3, the magnetic particles 48 cross the phase boundary, due to the centrifugal force, between the air 46 and the liquid 42, and are transported into the liquid 42.

In a subsequent phase 4, the fluidics structure 22 is positioned, in relation to the magnet 50, such that the magnet 50 is arranged adjacently to the radially inner area 24c of the second fluid chamber 24. Thus, the magnetic particles 48 are attracted to the magnet 50 across the phase boundary between the liquid 42 and the air 46, as is shown in FIG. 3e.

Subsequently, there is again, in a phase 5, an incremental rotation in small steps, as is indicated by arrows 60 in FIG. 3f, so that the magnetic particles 48 follow the magnet 50 and are transported into the radially inner portion 26b of the third fluid chamber 26 via the fluidic connection 34. Starting from the state shown in FIG. 3f, there will again be a rotation of the rotational body in the counter-clockwise direction in a phase 6 (not shown), so that the magnetic particles 48 are transported into the third liquid 44 across the phase boundary between the air 46 and the third liquid 44 due to the centrifugal force caused by said rotation.

Figure 3:
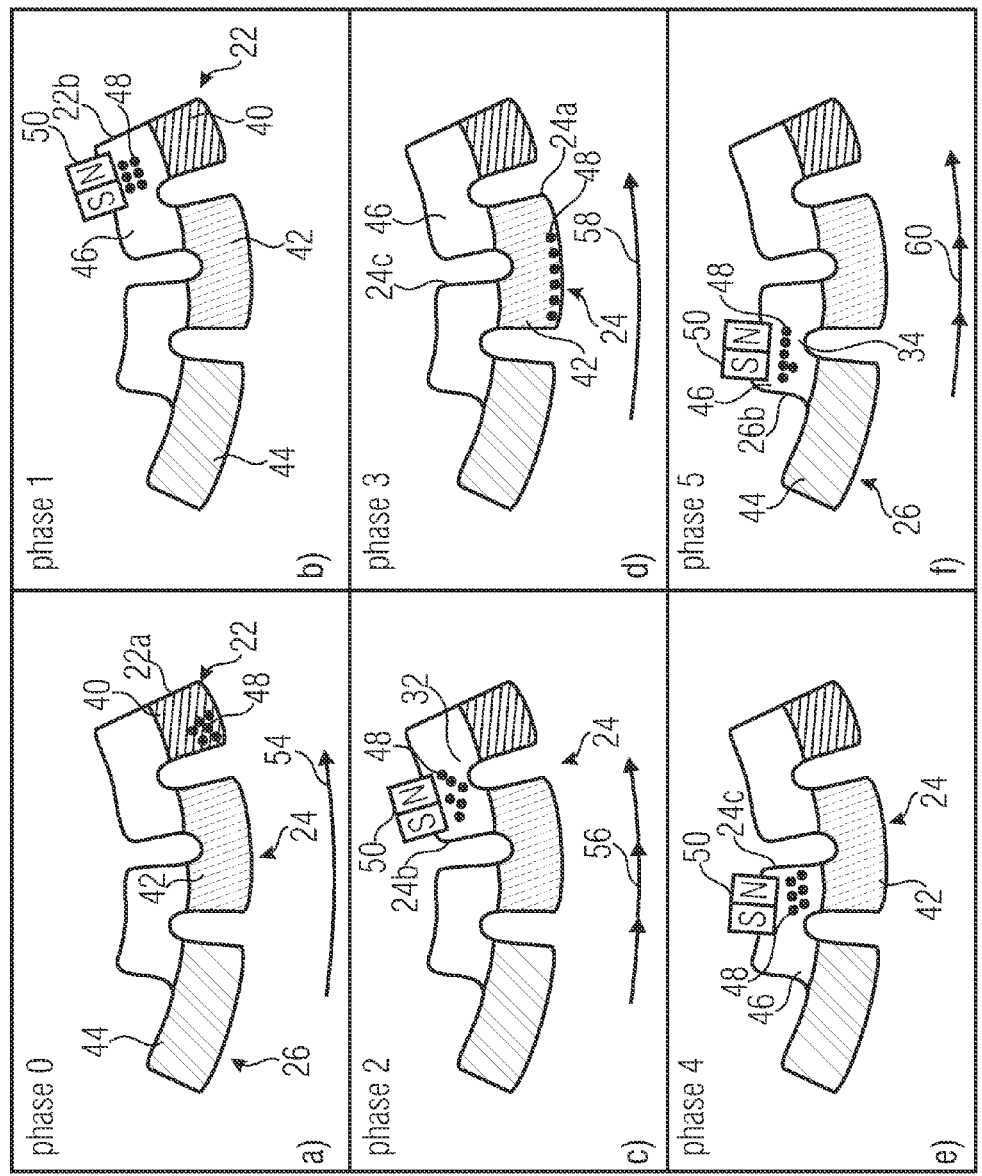
FIGS. 3a to 3f schematically show different phases during transport of magnetic particles while using a fluidics structure as is shown in FIG. 1.

With reference to FIG. 3, a sequential process of a transport of particles from a first fluid chamber into a third fluid chamber via a second fluid chamber has thus been described. In alternative embodiments, the mechanism presented may be used to transport particles between any number of chambers. The mechanism described enables iso-radial arrangement of the chambers—between which the particles are transported—in relation to an axis of rotation. Embodiments of the invention thus have reduced space requirements in the radial direction. Embodiments of the inventive transport mechanism thus enable entirely new approaches to transporting, isolating or concentrating different biomolecules such as proteins or nucleic acids, for example. Since the functionality is independent of the radial position, and since transport need not be directed radially outward, it is particularly suited for being implemented on a centrifugal-fluidic platform.

Embodiments of the invention thus enable effectively manipulating particles and/or transporting them between different liquid or gas phases, so that a high degree of automation may be achieved.

Embodiments of the invention relate, in particular, to utilization in DNA- and protein-based analytics, an essential part of which consists in isolating, cleaning up and possibly concentrating a target molecule or organism from a sample material. To this end, laboratories utilize, among other things, magnetic particles having application-specific surfaces as solid phases to which the target molecule, or the target organism, may attach in a targeted manner. By means of a magnet—due to their magnetizability—said particles subsequently have to be transferred, with the adhering target molecule/target organism, into a plurality of wash and elution solutions for further processing. Alternatively, it is possible to fix the particles in a laboratory vessel using an external magnet and to exchange the reagents. Such a process has so far been performed either manually or automatically while using a corresponding robot system; manual performance is error-prone, time-consuming and costly due to the multitude of pipetting steps, whereas devices for automation are very expensive, and are viable only in the case of high throughput.

In addition, both variants of implementation have the disadvantage of consuming large amounts of reagents. Embodiments of the inventive transport mechanism enable fully automatic mapping of corresponding laboratory protocols to a centrifugal-microfluidic diagnostics system. Due to the microfluidic realization, there is a potential for saving in terms of the amount of reagents used. For automating the transport, no expenses devices need to be procured, while at the same time, the error-proneness of the system decreases due to the automation, since no manual steps are necessitated for transporting the particles.

In embodiments, the structure shown may be employed, in connection with the transport mechanism described, for isolating, or extracting, nucleic acids from a crude lysate. Here, the first liquid 40 is a lysis or binding buffer, the second liquid 42 is a washing buffer, and the third liquid 44 is an eluting buffer. For said application, the magnetic particles 48 may have a silica surface to which DNA may unspecifically attach itself. The DNA would attach itself, in the first fluid chamber 22, to the silica surface of the particles. With the transport mechanism described, the particles are moved into the washing buffer in the second fluid chamber 24, where contamination is removed. By means of a further transport step, the particles are transferred into the third fluid chamber 26. The chemical properties of the eluting buffer result in that the attached DNA detaches from the particles and is now present in the eluting buffer in a free and cleaned-up state. Following the extraction, the isolated DNA may be amplified, for example, by a polymerase chain reaction (PCR). It has already been possible to validate a corresponding system for DNA extraction, in which case DNA was extracted from an *E. coli* lysate. A subsequent real-time PCR of the pal gene was able to demonstrate that the isolated DNA is sufficiently pure for further processing.

In a further form of application, the transport mechanism shown may be used for implementing a particle-based immunoassay. The latter may be performed in accordance with the following protocol, for example: the first fluid chamber 22 may be filled with a sample containing the substance to be detected. Magnetic particles having corresponding antibody or antigen coatings are added. The antibodies bind the substance to be detected. In a next step, the particles are transferred into the second fluid chamber 24, which contains a washing buffer, by means of the transport mechanism described. The particles are washed and transferred into the third chamber, which comprises a liquid having a detection antibody. During an incubation phase, the detection antibody attaches itself to the substance to be detected. The particles are then transferred into a fourth fluid chamber (not shown), which also contains a washing fluid, and eventually into a fifth fluid chamber, wherein a chemical reaction triggered by the detection antibody takes place.

In the above description, only those components were described which are necessitated for understanding the inventive transport mechanism. It is obvious to persons skilled in the art that corresponding fluidics structures may be provided for supplying the corresponding liquids and the magnetic particles. Also, further fluidics structures may be provided upstream or downstream from the fluidics structure represented.

In embodiments of the present invention, a rotating substrate comprising a plurality of microfluidic chambers is thus provided, the chambers being connected on the radially inner side, and the connection being filled with air, for example. On the radially outer side, the chambers are separated via a fluidic barrier. A static magnet or several magnets that are external to the rotating substrate are provided, so that transport of magnetic particles across a phase boundary is possible in an idle state when the rotating substrate is positioned accordingly. During rotation of the rotating substrate, the centrifugal force may predominate over the magnetic force, so that the magnetic force has no influence on the particles. The chambers may be iso-radially arranged and need not be connected in series. In embodiments of the invention, a plurality of corresponding fluidics structures may be arranged on a disk such that they are azimuthally distributed, it being possible for one or more magnets to be provided correspondingly for each fluidics structure.

In embodiments of the invention, the magnetic particles, which may also be referred to as magnetic microelements, may be ferro-, para-, or super-paramagnetic particles. In embodiments, the centrifugal-microfluidic platform, i.e. the rotational body, may be a platform made of a plastic film, for example of COC (cyclic olefin copolymer), COP (cyclic olefin polymer), PMMA (polymethyl methacrylate), PS (polystyrene) or PC (polycarbonate). Alternatively, the centrifugal-microfluidic platform may be plastic disk made of the (thermoplastic) plastics mentioned. In embodiments of the invention, the magnet may be a permanent magnet, whereas in alternative embodiments, the magnet may be an electromagnet. The magnetic particles may be configured to enable adhesion of biological molecules such as DNA, proteins or antibodies, for example. In embodiments, identical liquids or different liquids may be provided within the various fluid chambers. Air, a gas or any other substance which does not mix with the liquids within the respective fluid chambers may be contained within the fluidic connections which connect radially inner portions of the fluid chambers. The cavities of the chambers may be provided with a hydrophobic coating, for example teflon in a solvent, or with a hydrophilic coating. Alternatively, the cavities of the chambers may be provided with a coating for blocking, for example BSA.

In the embodiment described, the radially inner portion of the second fluid chamber 24 comprises two areas 24*b* and 24*c* that are separated from each other by a barrier 30. In alternative embodiments, the barrier 30 need not be provided. However, the barrier 30 is advantageous in that it reliably ensures that no magnetic particles may enter into the third liquid 44 while bypassing the second liquid 42.

In other words, embodiments of the present invention thus provide a substrate comprising a plurality of (microfluidic) chambers that are separated in a radially outer position and are connected in a radially inner position; the chambers that may be iso-radially arranged are filled with identical or different liquids, and the liquids are not in fluidic contact with one another, the substrate is rotatable about an axis, and magnetic particles can be transported between the chambers across a phase boundary (liquid/gas) by suitably arranging at least one magnet mounted outside the substrate. Upon rotation, the magnetic field has no significant influence on the magnetic particles, since the centrifugal force is considerably predominant and since the radial sphere of influence of the magnet is sufficiently low or the fluidic resistance of the liquid is too high. In the idle state of the substrate, given a corresponding position relative to the magnet, the particles are moved toward the magnet and across a phase boundary, the particles being moved outward again upon subsequent rotation due to the centrifugal force. By suitably combining the steps mentioned, it is possible to transport particles from a chamber filled with a first liquid into a chamber filled with a second liquid while transporting them via a gap not filled with liquid.

In other words, embodiments of the present invention provide a method and a device for transporting magnetic microelements on a microfluidic platform which is rotatable about an axis, the platform having a plurality of fluidic chambers located thereon which are iso-radially arranged and which are connected to one another on the radially inner side, the chambers being filled with a liquid medium, and the connecting area being filled with a medium of a different density which is not miscible with the medium contained within the other chambers, such as air, for example. At least one of the chambers has magnetic microelements located therein which—due to corresponding positioning of the microfluidic platform relative to an external, stationary magnet—move toward same (across a phase boundary). Upon rotation of the microfluidic platform, the magnet has a negligible influence on the particles in one of the microfluidic chambers due to the centrifugal force or due to the low magnetic sphere of influence. By suitably combining the above-mentioned steps, particles may be transferred from a first chamber into a second chamber.

The present invention offers numerous advantages over the conventional technology known. Embodiments of the invention may be employed in a very flexible manner, for example as a transport mechanism both for nucleic acid-based and protein-based analytics and possibly for many other applications. Depending on the application desired, particles may have different surface functionalizations. In addition, the number of fluidic chambers is readily adaptable and expandable, without there being any space requirement in the radial direction.

Embodiments of the invention have low system requirements, a functionality existing already at rotational frequencies of less than 7 Hz. Only one rotational direction is needed. Embodiments of the invention may be implemented independently of a substrate material, film or milled disks being employable, for example. In embodiments, no active actuation of magnets is necessitated, so that no corresponding movable parts are necessitated. Furthermore, no magnet is necessitated in the rotational body, so that same may be produced at low cost and in a simple manner.

Embodiments of the invention allow the particles to be transported across a liquid/gas interface, so that no cross-over of liquids takes place. In contrast to application in laboratories, in embodiments of the invention particles are transported from liquid to liquid, whereas in laboratories the particles are often fixed by means of only one magnet, and the liquid is exchanged, in which case fluid residues remain which may result in subsequent contamination.

Even though embodiments comprising two or three chambers, between which magnetic particles are transported, were specifically described, it is readily obvious to persons skilled in the art that, in accordance with the invention, magnetic particles may be transported between any number of chambers, as may be necessitated for performing examinations, analyses and assays.

In embodiments, the fluid chambers are suitably configured to be able to reliably prevent cross-contamination of liquids between fluid chambers. In embodiments of the invention, a barrier provided between adjacent fluid chambers may have a radial height of more than 200 µm or more than 500 µm. In embodiments of the invention, the fluid chambers are filled with liquid up to a specific radial height only, so that an overflow of liquid through the radially inner fluidic connection between fluid chambers will not take place.

Further disclosed is a device for transporting magnetic particles, comprising: a rotational body configured for a rotation about an axis of rotation; a fluidics structure within the rotational body, said fluidics structure comprising at least first and second fluid chambers, the first and second fluid chambers comprising a fluidic connection in a portion which is located radially inward in relation to the axis of rotation, and being fluidically separated from each other in a portion which is located radially outward in relation to the axis of rotation; and a magnetic-force element configured to exert, as a function of a positional relationship between the magnetic-force element and the fluidics structure, a magnetic force on magnetic particles arranged in the fluidics structure; and a drive configured to subject the rotational body to rotation about the axis of rotation, the positional relationship between the magnetic-force element and the fluidics structure being adjustable as a result; and a controller designed to control the drive, in a first phase, such that the first fluid chamber is arranged in relation to the magnetic-force element in such a manner that, due to the magnetic force, magnetic particles are transported from a liquid arranged in the radially outer portion of the first fluid chamber into the radially inner portion of the first fluid chamber; to control the drive, in a second phase, such that a change in the positional relationship between the fluidics structure and the magnetic-force element is effected such that, due to the magnetic force, the magnetic particles are transported through the fluidic connection between the first and second fluid chambers into the radially inner portion of the second fluid chamber; and to control the drive, in a third phase, such that the rotational body is subjected to such rotation that the magnetic particles are transported, by means of centrifugal force, from the radially inner portion of the second fluid chamber into a liquid arranged in the radially outer portion of the second fluid chamber, said liquid not being in fluidic contact with the liquid in the first fluid chamber.

In such a device, the radially outer portions of the first and second fluid chambers may be separated by a radially inwardly projecting barrier which has a radial height of more than 200 µm or more than 500 µm.

In such a device, a gas may be arranged in the radially inner portion of the first and second fluid chambers.

In such a device, the liquid in the radially outer portion of the first fluid chamber and the liquid in the radially outer portion of the second fluid chamber may be different liquids.

In such a device, the fluidics structure may comprise at least one third fluid chamber, the second and third fluid chambers comprising a fluidic connection in a portion which is located radially inward in relation to the axis of rotation, and being fluidically separated from each other in a portion which is located radially outward in relation to the axis of rotation, the controller being designed to control the drive, in a fourth phase, such that the second fluid chamber is arranged in relation to the magnetic-force element in such a manner that, due to the magnetic force, the magnetic particles are transported from the liquid in the radially outer portion of the second fluid chamber into the radially inner portion of the second fluid chamber; to control the drive, in a fifth phase, such that a change in the positional relationship between the fluidics structure and the magnetic-force element is effected such that, due to the magnetic force, the magnetic particles are transported through the fluidic connection between the second and third fluid chambers into the radially inner portion of the third fluid chamber; and to control the drive, in a sixth phase, such that the rotational body is subjected to such rotation that the magnetic particles are transported, by means of centrifugal force, from the radially inner portion of the third fluid chamber into a liquid arranged in the radially outer portion of the third fluid chamber, said liquid not being in fluidic contact with the liquid in the second fluid chamber.

In such a device, the liquid in the radially outer portion of the second fluid chamber and the liquid in the radially outer portion of the third fluid chamber may be different liquids.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

I claim:

1. Method of transporting magnetic particles while using a device comprising:
    a rotational body configured for a rotation about an axis of rotation;
    a fluidics structure within the rotational body, said fluidics structure comprising at least first and second fluid chambers, the first and second fluid chambers comprising a fluidic connection in a portion which is located radially inward in relation to the axis of rotation, and being fluidically separated from each other in a portion which is located radially outward in relation to the axis of rotation; and
    a permanent magnet configured to exert, as a function of a positional relationship between the permanent magnet and the fluidics structure, a magnetic force on magnetic particles arranged in the fluidics structure; and
    a drive configured to subject the rotational body to rotation about the axis of rotation, the positional relationship between the permanent magnet and the fluidics structure being adjustable as a result,
    the method comprising:
        in a first phase, arranging the first fluid chamber in relation to the permanent magnet in such a manner that, due to the magnetic force, the magnetic particles are transported from a liquid arranged in the radially outer portion of the first fluid chamber into the radially inner portion of the first fluid chamber;
        in a second phase, changing the positional relationship between the fluidics structure and the permanent magnet by rotating the rotational body such that, due to the magnetic force, the magnetic particles are transported through the fluidic connection between the first and second fluid chambers into the radially inner portion of the second fluid chamber; and
        in a third phase, subjecting the rotational body to such rotation that the magnetic particles are transported, by means of centrifugal force, from the radially inner portion of the second fluid chamber into a liquid arranged in the radially outer portion of the second fluid chamber, said liquid not being in fluidic contact with the liquid in the first fluid chamber,
    wherein in the first phase, the magnetic particles are transported across a phase boundary between the liquid in the radially outer portion of the first fluid chamber and a gas in the radially inner portion of the first fluid chamber, and wherein in the third phase the magnetic particles are moved across a phase boundary between a gas in the radially inner portion of the second fluid chamber and the liquid in the radially outer portion of the second fluid chamber,
    wherein the adjustment of the positional relationship of the permanent magnet and the fluidics structure, which results in the transport of the magnetic particles due to the magnetic force, is effected by rotating the rotational body.

2. Method as claimed in claim 1, wherein the radially outer portions of the first and second fluid chambers are separated by a radially inwardly projecting barrier which comprises a radial height of more than 200 μm or more than 500 μm.

3. Method as claimed in claim 1, wherein the liquid in the radially outer portion of the first fluid chamber is different from the liquid in the radially outer portion of the second fluid chamber.

4. Method as claimed in claim 1, wherein the fluidics structure comprises at least one third fluid chamber, the second and third fluid chambers comprising a fluidic connection in a portion which is located radially inward in relation to the axis of rotation, and being fluidically separated from each other in a portion which is located radially outward in relation to the axis of rotation, the method comprising:
    in a fourth phase, arranging the second fluid chamber in relation to the permanent magnet in such a manner that, due to the magnetic force, the magnetic particles are transported from the liquid in the radially outer portion of the second fluid chamber into the radially inner portion of the second fluid chamber;
    in a fifth phase, changing the positional relationship between the fluidics structure and the permanent magnet such that, due to the magnetic force, the magnetic particles are transported through the fluidic connection between the second and third fluid chambers into the radially inner portion of the third fluid chamber; and
    in a sixth phase, subjecting the rotational body to such rotation that the magnetic particles are transported, by means of centrifugal force, from the radially inner portion of the third fluid chamber into a liquid arranged in the radially outer portion of the third fluid chamber, said liquid not being in fluidic contact with the liquid in the second fluid chamber.

5. Method as claimed in claim 4, wherein the liquid in the radially outer portion of the second fluid chamber and the liquid in the radially outer portion of the third fluid chamber are different liquids.

6. Method as claimed in claim 1, wherein the radially inner portion of the second fluid chamber comprises a first area and a second area between which a barrier is arranged and which are fluidically connected via the radially outer portion of the second fluid chamber.

7. Method as claimed in claim 6, wherein in the third phase the magnetic particles are transported, due to the rotation, from an area of the radially outer portion, said area being adjacent to the first area of the radially inner portion, into an area of radially outer portion which is adjacent to the second area of the radially inner portion.

8. Method as claimed in claim 1, wherein the fluid chambers comprise areas which overlap in the direction that is azimuthal in relation to the axis of rotation.

9. Method as claimed in claim 8, wherein the fluid chambers are iso-radially arranged in relation to the axis of rotation.

10. Method as claimed in claim 1, wherein in the second phase the drive of the rotational body is subjected to such incremental rotation that the magnetic force is higher than the centrifugal force caused by the rotation, so that the magnetic particles are transported, following the permanent magnet, through the fluidic connection between the radially inner portions of the first and second fluid chambers in an essentially azimuthal direction due to the magnetic force.

\* \* \* \* \*